United States Patent [19]

Russek

[11] 4,381,012

[45] Apr. 26, 1983

[54] ELECTRODE PLACEMENT DEVICE

[75] Inventor: Allen S. Russek, Medford, N.Y.

[73] Assignee: Wallant International Trade, Inc., New York, N.Y.

[21] Appl. No.: 190,242

[22] Filed: Sep. 24, 1980

[51] Int. Cl.³ .............................................. A61B 5/04
[52] U.S. Cl. .................................... 128/644; 128/802
[58] Field of Search ........ 128/639, 644, 783, 791–793, 128/798, 799, 802

[56] References Cited

U.S. PATENT DOCUMENTS

| 3,409,007 | 11/1968 | Fuller | 128/644 |
| 3,534,727 | 10/1970 | Roman | 128/644 |
| 3,612,061 | 10/1971 | Collins et al. | 128/799 |
| 3,888,240 | 6/1975 | Reinhold, Jr. et al. | 128/644 |
| 3,971,387 | 7/1976 | Mantell | 128/792 |
| 3,998,213 | 12/1976 | Price | 128/644 |
| 4,121,575 | 10/1978 | Mills et al. | 128/644 |
| 4,202,344 | 5/1980 | Mills et al. | 128/644 |

OTHER PUBLICATIONS

TENS-PAC, Instructions for Use, Model D, Catalog No. 1010-0001 Transcutaneous Electrical Nerve Stimulator, Dow Corning Wright.
Petrucelli et al., "A Serial to Parallel . . . TENS Pain Suppression", Proceedings of 7th N. E. Bioeng. Conf., Mar. 22-23, 1979, pp. 388-390.

Primary Examiner—Lee S. Cohen
Attorney, Agent, or Firm—Frishauf, Holtz, Goodman & Woodward

[57] ABSTRACT

A device for placement against a body and for locating at least one electrode at a predetermined portion of a body includes a first portion to which at least one electrode is secured at at least one of a plurality of positions thereon, and electrical connectors coupled to the first portion for electrically connecting the at least one electrode to an electrical signal receiving and/or generating apparatus. The device is removably secured to the body of a wearer with a predetermined automatic orientation so that the at least one electrode is properly located adjacent a body portion of the wearer. A touch sensitive locating device is provided on the device for positively orienting the device relative to a predetermined body portion of the wearer to insure proper electrode placement against the body.

33 Claims, 19 Drawing Figures

ELECTRODE PLACEMENT DEVICE

BACKGROUND OF THE INVENTION

This invention relates to an electrode placement device for automatically placing and securing electrodes for transcutaneous nerve stimulation, monitoring of body functions, etc.

At present, transcutaneous nerve stimulation (hereinafter referred to as TENS) to relieve pain is carried out by placing electrodes on specific body portions of the patient. The precise locations of the electrodes is critical for best results. When using a TENS device in connection with management of pain, it is time consuming for a practitioner to locate the electrodes at proper points on the patient to provide the desired pain relieving results. Moreover, after the patient leaves the practitioner's office and takes the TENS device home, it is extremely difficult for the patient, using present-day devices and electrodes, to locate by himself the correct locations for placement of the electrodes to provide best pain relieving results. Particular considerations apply with respect to the shoulder, neck, upper and lower back areas and other areas of the body which are neither visible nor normally accessible for self placement of the electrodes, especially for people who are in pain and who may have limited body movement capabilities.

It is extremely difficult for the patient to secure the electrodes at the proper location sites. Current practice is to utilize adhesive tape patches over the electrodes, adhesive coated electrodes or strips of adhering paper using 3M adhesive preparations trademarked Dermacil and Micropore ® which adhere to the skin. The electrodes must be secured for many hours since the devices are used intermittently throughout the day and transported by the patient connected to the body. Suction cup and other self adhering electrodes will not remain attached to the body for necessary time periods. When using TENS and related electronic devices, the patient is cautioned against continued use if skin rash or irritation is caused by the adhesive. The present invention eliminates the need for adhesives and possible side effects from their usage.

In some cases, it is difficult for the practitioner to even find the proper locations for placement of the electrodes on the patient's body. The present invention has been designed to obviate or reduce this difficulty.

While the above description is given with respect to TENS devices, similar considerations also apply for various other electronic devices requiring electrode placement at specific body locations. Throughout the following specification, only TENS devices will be discussed, it being apparent that various other electronic devices which require electrode placement on the body are within the scope of this disclosure.

The object of the present invention is to provide a device which permits automatic accurate and easy location of electrodes on the body of the patient for use with, for example, TENS devices or other electronic devices requiring continuously secure and accurate electrode placement against the body of a patient. It is also an object that the patient can repeatedly achieve such accurate electrode placement after leaving the practitioner's office.

A further object of the invention is to provide such a device which enables electrodes to be accurately located at specific body locations in a simple, repeatable and expedient manner.

A further object of the invention is to provide such a device which enables a great variety of electronic stimulation points to be selected so that the device may be used for multiple purposes.

Yet another object of the invention is to provide such a device which is simple in construction reliable, long lasting easily adjustable and which may be laundered or otherwise cleaned so as to keep it in a sanitary condition. It may be made of one or more parts which may be easily detached from each other.

SUMMARY OF THE INVENTION

In accordance with the present invention, a device for continuously secure placement of electrodes against a body of a wearer, and for automatically locating at least one electrode at a predetermined location adjacent the body of a wearer, comprises a first portion which is adapted to be placed against a body portion of a wearer, the first portion having at least one electrode at at least one of a plurality of positions thereon, and means for electrically connecting the at least one electrode to an electrical signal generating and/or receiving device. Further provided is means for removably securing the device to the body of the wearer with the at least one electrode adjacent to a predetermined body portion of the wearer. A locating means is provided on the device for cooperating with a predetermined body portion of the wearer for positively locating the device relative to the predetermined body portion, thereby insuring that the device is positively located with the at least one electrode adjacent to the body at the proper position on the body of the wearer.

DETAILED DESCRIPTION

Figures 1, 1A, 2, 3:
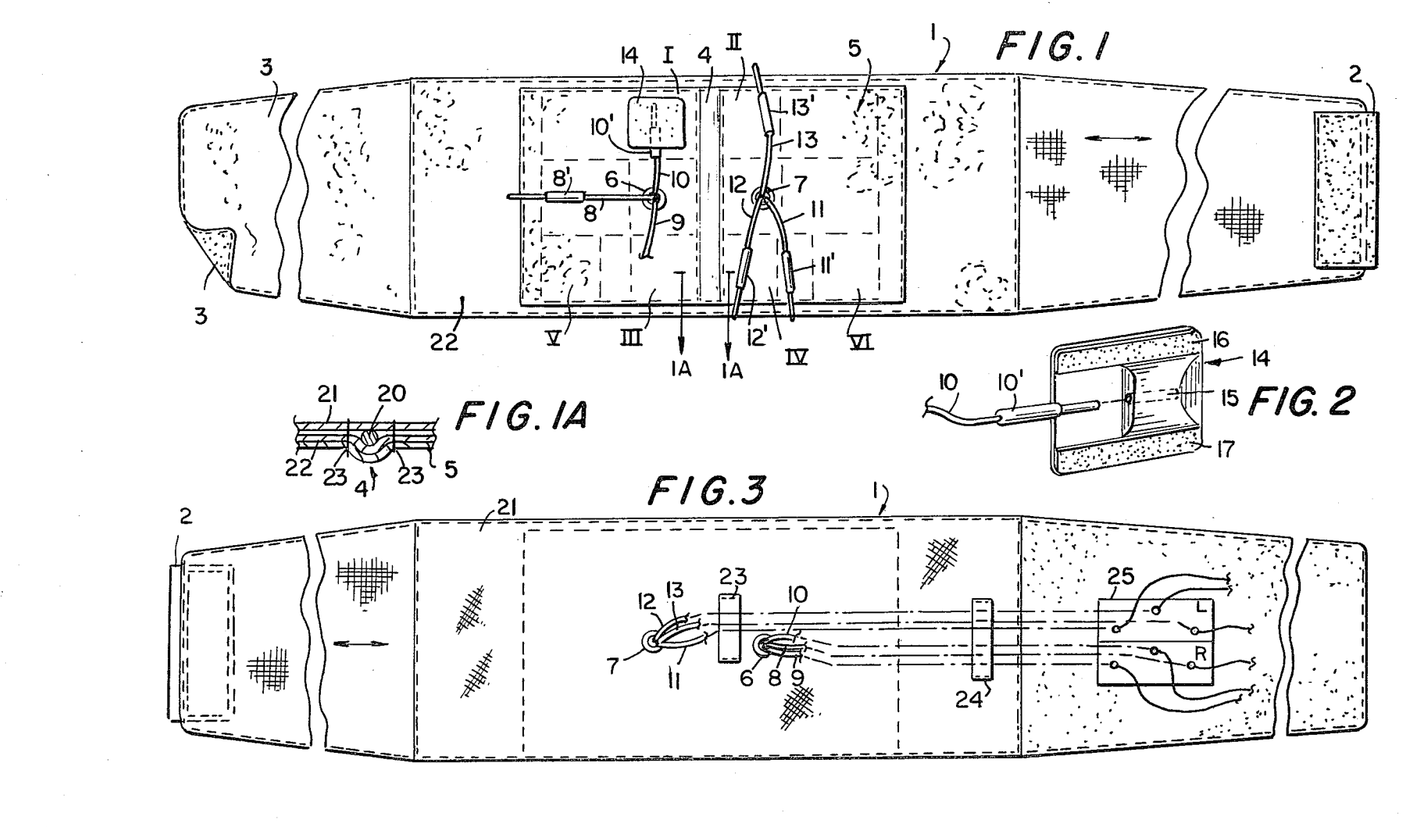
FIG. 1 is a view of the inside portion of a belt-like device for use in locating electrodes in the vicinity of the lower back.
FIG. 1A is an exploded sectional view of the portion designated 1A—1A in FIG. 1.
FIG. 2 is an exploded view of a typical electrode for use with the device of FIG. 1.
FIG. 3 is an outside view of the device of FIG. 1.

Referring to FIGS. 1-3, a belt-like electrode placement device 1 is made of a fabric which is preferably washable and/or dry cleanable. Secured at one end of the fabric is a hook-type Velco connector 2, the hooks of which face inwardly of the garment. At the other end of the garment is a loop-type Velcro fastener material 3, on the outer side of the garment, for adjustable connection with the hook-type Velcro fastener portion 2.

Located centrally of the device is a touch sensitive locator portion 4 which may be a stiffened and/or protruding portion as shown in FIG. 1A. This locating portion 4 is provided so that the patient may align same with, for example, the spine, thereby insuring that the device is properly located on the body of the patient each time it is used, so that electrode placement will be consistently repeatable. Locating portion 4 in FIGS. 1 and 1A comprises a fabric or other filler member 20 located between layers 21, 22 of the belt, seams 23 keeping the members in relative position. The locating portion 4 may protrude inwardly (FIG. 1A) and/or outwardly of the device. Locating portion 4 may instead comprise a rough, but non-irritating fabric portion or layer which is placed and located against, for example, the spine. In this case it is not necessary for portion 4 to protrude.

The central inner portion of the device includes a further loop-type Velcro fastening area 5 on which electrodes are to be placed at various specified locations. The drawing illustrates six locations I-VI. It should be clear that more or fewer specified electrode placement locations could be provided, six being shown merely by way of example. The six locating areas are preferably visually designated on the Velcro area 5, for example by imprinting or other technique, so that the patient and physician will be able to precisely locate the electrodes thereon. The indicated electrode locations apply to substantially all or most body configurations. Alternatively, the Velcro portion 5 may be provided in a blank state, the physician outlining or marking the specified electrode locations, for example with a marking pen, or the like, after the specific locations for a given patient have been determined. This need only rarely be done since the pre-indicated locations are correct for almost all people. The six locations are generally used in pairs, two cooperating electrodes being used in respective pairs. For example, two electrodes placed at respective locations I and II may constitute a pair, electrodes at respective locations III and IV may constitute a pair, etc. For dual channel TENS devices, two pairs of electrodes may be simultaneously used.

The belt of FIG. 1 has electrical wires 8-13 extending therethrough, between fabric layers 21,22, the electrical wires extending out in FIG. 1 through grommets 6,7. Other techniques for passing the wires through the belt could be used, as desired and as expedient in specific applications. The wires 8-13 each have respective plugs 8'-13' at the ends therefor for connection with electrodes such as electrode 14 which is shown in greater detail in FIG. 2. Electrode 14 is a conventional type of electrode made of electroconductive flexible preferably rubber-like material and having a receptacle 15 therein for receiving a plug such as plug 10' as shown in FIG. 2. Electrodes of the type generally shown in FIGS. 1 and 2 are designated in the trade as, for example, flexible carbon electrodes. Such electrodes are from, for example, Uni-Patch Inc., Wabash, Minnesota. The electrode 14 also has hook-type Velcro fasteners 16,17 on the rear surface thereof for adjustable engagement with the loop-type Velcro surface 5 so that it may be adjustably placed any way on surface 5. Fasteners 16,17 may be sewn onto electrodes 14, or may be attached by an appropriate adhesive. Any desired number of electrodes 14 may be used, depending upon the treatment desired and the capacity of the electronic device, such as a TENS device, to which the electrodes are connected. Only one electrode 14 is illustrated in FIG. 1 for ease of illustration. The portion of the device carrying the electrodes is substantially non-stretchable, consistent with the aforementioned object of the invention to provide precise and repeatable orientation of the electrodes on the body of the user.

As shown in FIG. 3, the wires 8-13 pass through the grommets 6,7 and extend between the fabric layers 21,22 of the device. Wire locating loops 23,24, which are preferably pieces of fabric stitched to one or the other of fabric layers 21,22, are provided to guide the wires 8-13 toward the end portion of the belt. The wires 8-13 extend to a plate 25 and pass therethrough so as to be fed to an electronic device, such as a TENS device. The plate 25 has left (L) and right (R) designations thereon, and also includes numberings for the various wires so that they may be easily identified for connection to the electronic input device. Details of how the wires 8-13 are connected to the electronic device such as a TENS device, are omitted since they are readily apparent to those skilled in the art to which the present invention pertains.

Figure 4:
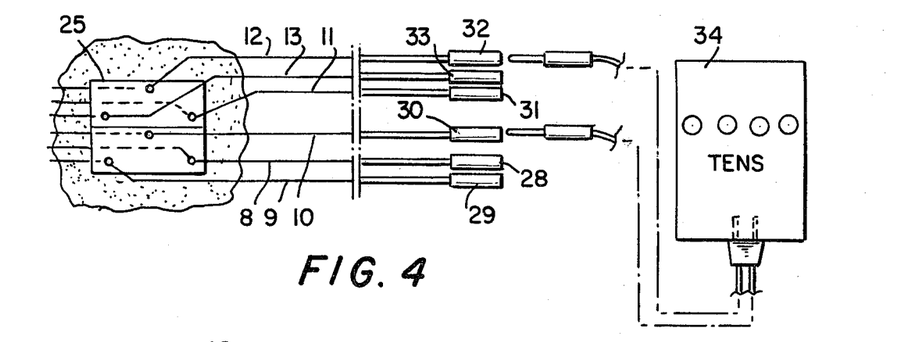
FIG. 4 is an exploded view of the connector portion of the device of FIGS. 1 and 3, showing how the device is electrically connected to an electronic device, such as a TENS device.

FIG. 4 illustrates how the wires 8-13 extend from the plate 25 and, in the illustrated embodiment, have sockets or receptacles 28-33, respectively at the ends thereof for connection to plugs of an electronic device, such as a TENS device 34 for energization of electrodes of the belt-like device. The TENS device 34 is shown with only two electrical wires extending therefrom. However, a dual channel device having four wires can be used, as desired.

Figure 5:
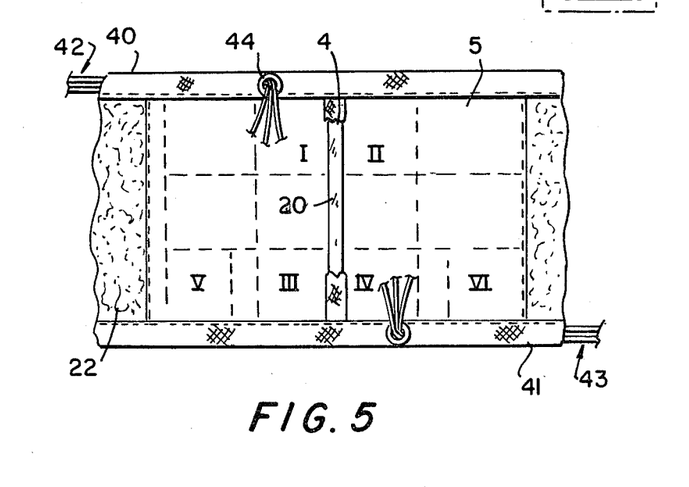
FIG. 5 is an inner or body-side view of a modified device.
Figure 6:
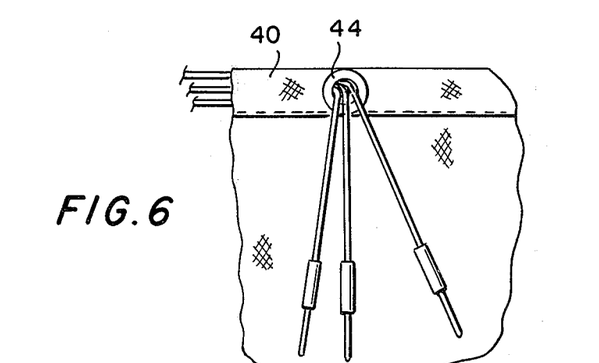
FIG. 6 is an exploded view of the device of FIG. 5 showing how connections are made to an electrode.

FIGS. 5 and 6 illustrate a modified device having a loop-like seamed arrangement 40,41 between the fabric layers 21,22 so as to provide a channel through which wires generally designated 42,43 may pass for connection between an electronic device and electrodes. As shown in the exploded view of FIG. 6, the wires preferably pass through a grommet 44 or other opening in the passageways or channels 40,41 and may have respective plugs at the ends thereof. The plugs may connect to electrodes in a similar manner as in FIGS. 1-4.

FIG. 5 illustrates the wires 42,43 extending in opposite directions of the belt so that the left and right channels may be more easily identified by the user. The wires may alternatively extend in the same direction on the belt so that they emerge on the same side of the patient. Still further, instead of having channels at the top and bottom of the belt, all of the wires may extend through one channel, located at the top or the bottom of the belt, as desired. The external connections may be made as illustrated in FIG. 4, or as in subsequent embodiments.

Figure 7:
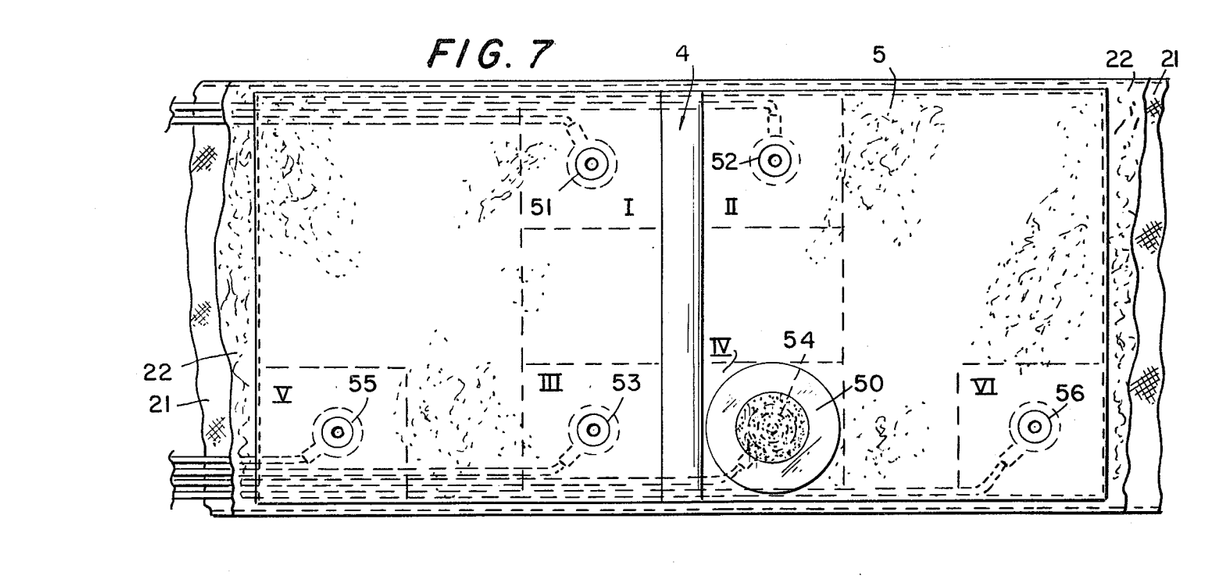
FIG. 7 is a partial inner or body side view of a further modified device for use with different type electrodes.
Figure 8:
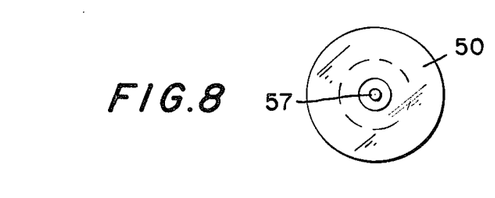
FIG. 8 is a rear view of a snap-type electrode for use with the device of FIG. 7.

FIGS. 7 and 8 illustrate a further modified arrangement for use with snap-type electrodes 50. In FIG. 7, elements which are the same or similar to those elements shown in FIGS. 1–3 are given the same reference numerals. In FIG. 7, the wires leading to the various electrode locations are internal of the belt layers, for example as shown in FIG. 7, or may be shown in FIG. 3 or FIG. 5. The wires extend to snap-like connectors 51–56, respectively, for making electrical connection to a snap-type electrode 50. The rear or snap portion 57 of electrode 50 is shown in FIG. 8. Electrical connections to the wires are made in a manner as shown, for example, in FIG. 4, or in accordance with modified arrangements discussed hereinbelow. In use, the electrodes 50 are snapped onto the desired snaps 51–56, and appropriate electrical connections are made to the wires associated with the respective snaps on which electrodes have been connected. The electronic device connected to the respective wires activates the electrodes to provide the desired results. Electrodes such as electrode 50 are at present readily available in various different forms, for example flexible carbon electrode form, and are not discussed further in detail. As mentioned above, with present-day TENS devices, the electrodes are used in pairs (i.e., I–II; III–IV; and/or V–VI).

Figure 9:
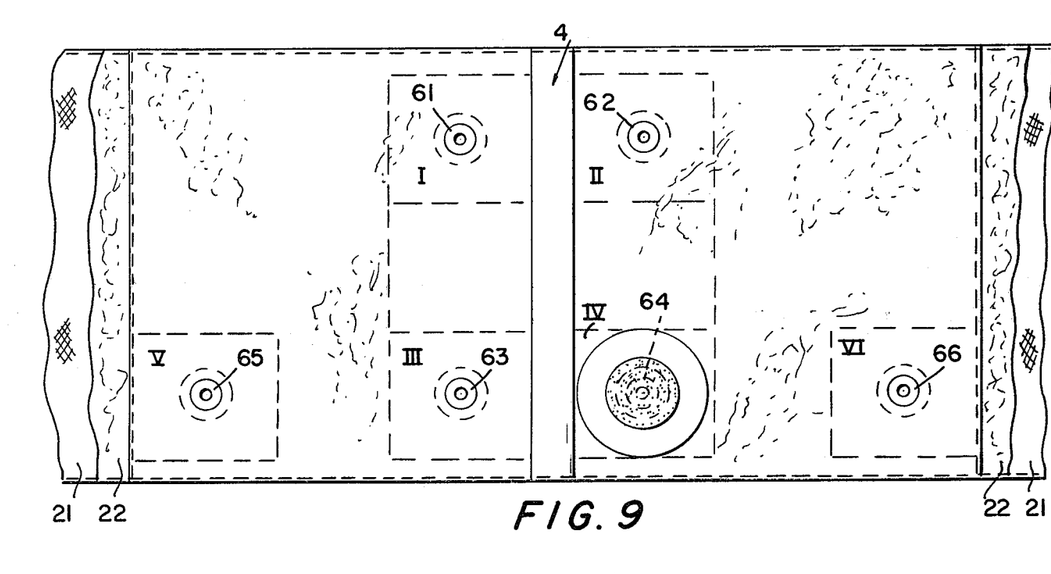
FIG. 9 is a partial view of the inner or body side of a further modified device of the present invention.
Figure 10:
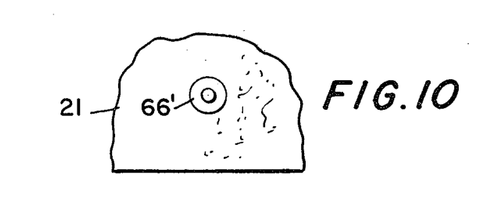
FIG. 10 is a partial outer view of the device of FIG. 9.

FIG. 9 illustrates a modified arrangement wherein no wires at all are provided in the belt-like device. In the arrangement of FIG. 9, the snap-type connectors 61–66 extend to the inner surface of the belt (the side which is against the patient's body) for connection of an electrode thereto. The snap-like connectors are preferably fabricated so that they also extend to the outer side of the belt, for example as shown in FIG. 10, with a male snap-type connector 66', so that an energization wire from an electronic device, such as a TENS device, can be snap-connected thereto to energize the snap-connectors to which they are connected. FIG. 10 is a fragmentary view of the outer portion of the garment and shows only one snap-type connector extending outwardly of the belt which is integral or otherwise fixedly connected with snap-type connector 66. Alternatively, as shown in FIG. 11, the snap-type connectors 61–66 may be respectively connected to jacks or receptacles 66" which extend to the outside of the belt-like device and which receive respective plugs of an electronic device for energization.

Figure 11:
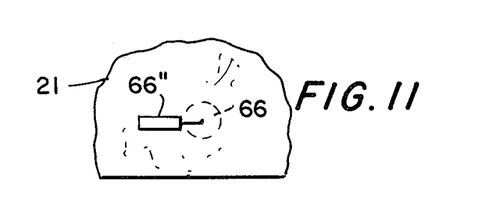
FIG. 11 is a partial outer view, similar to the outer view of FIG. 10 showing a modified arrangement of the invention.

The embodiments of FIGS. 9–11 may be made of only a single layer of fabric since no wires are running internal thereof. This type of arrangement is advantageous from the laundering or cleaning point of view since there is a minimal number of wires which could be damaged. The arrangement of FIGS. 9 and 10 is particularly advantageous since no wires at all are present in the belt, per se.

In the embodiments previously described wherein the wires run internal of the belt, it should be clear that the wires could also be routed externally of the belt, through, for example, guiding loops. This arrangement, however, is less preferred than the previously described arrangements since the wires are exposed and are more prone to damage, tangling, etc.

As a further modification, an electronic or TENS device may be mounted directly to the belt generally in the vicinity of connecting plate 25 so that the wires from the TENS device are routed directly to the belt for connection to the electrodes. If desired, connectors, such as snap or plug-in type connectors can be used to attach the TENS device directly to the belt.

Figure 12:
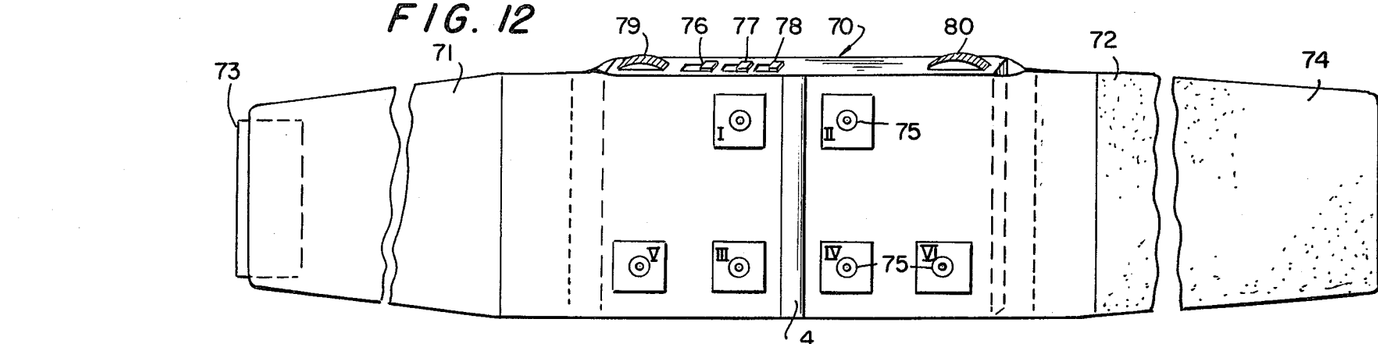
FIGS. 12 and 13 illustrate further modified embodiments of the invention.
Figure 13:
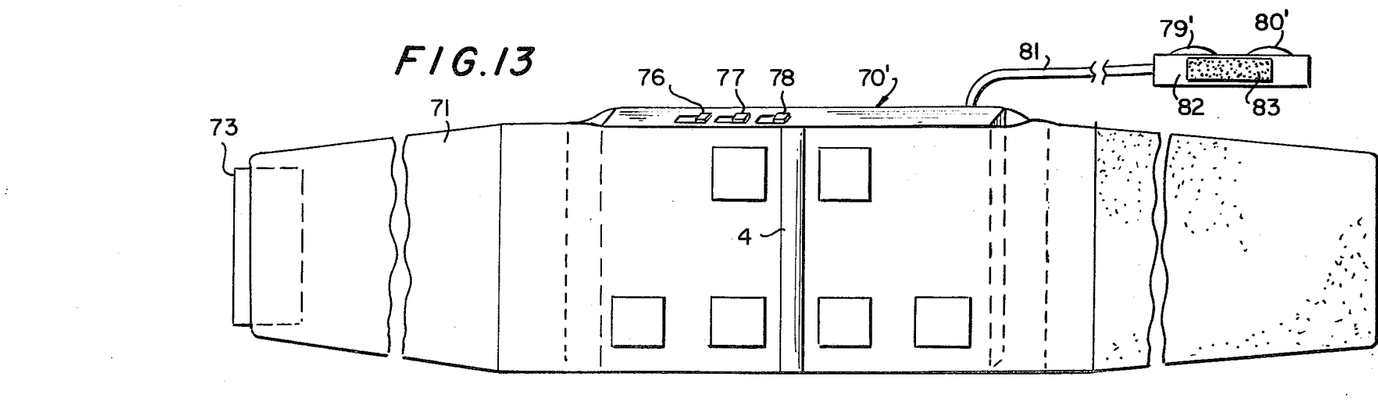

FIGS. 12 and 13 illustrate a further modification of the invention whereby the complete TENS device is an integral portion of the electrode locating and retaining device.

Referring to FIG. 12, a miniaturized TENS device formed in a flat-pack type arrangement 70 has flexible fabric or fabric-like members 71,72 with Velcro closures 73,74 respectively mounted at the ends thereof so that the device forms a belt-like arrangement. The TENS device is preferably formed of resilient plastic material so that it may be bent to conform to the back or other body portion of the patient. The TENS device 70 has electrode connector snaps 75 at positions I–VI for snap-connection to electrodes. As in the previous embodiments, the electrodes are preferably used in pairs. Switches 76,77,78 control the energization of the pairs of electrode snap connectors 75 so that the appropriate body portions are applied with electrical signals from the TENS device. An amplitude and on/off control knob 79 is provided for one channel of the TENS device. If a second channel is provided, a second on-off amplitude control knob 80 is provided for the second channel. Adjustments for pulse rate and pulse width are preferably not available to the patient and are practitioner adjusted, for example by means of screw driver operated controls (not shown). The TENS device 70 may be energized by internally contained flat-pack type batteries, or may be connected to an external battery pack which may be carried by the patient and connected to the device by means of wires. The touch sensitive locating means 4 can be either a raised portion (as illustrated in FIGS. 1–3) or may be a surface area portion of TENS device 70 which is roughened, but not irritating to the patient, or it may be some other type of surface which may be easily discerned by the patient and properly located against the body.

In a modified arrangement, as shown in FIG. 13, the TENS device 70' only has switches 76–78 thereon, the amplitude—on/off controls 79',80' being provided remote from the TENS device. The amplitude controls 79',80', for the two channels, are connected to the TENS device 70' by means of a cable 81. The control housing 82 may be attached to the belt portion 72 in a convenient location, or may be attached or located elsewhere on the patient. This arrangement is particularly advantageous to enable more convenient control by a patient who has limited movement and cannot reach behind his back, for example, to adjust amplitude or turn the unit on and off. The control housing 82 may be attached to the belt portion 72 by means of, for example, Velcro fastener 83 and associated Velcro fastening portion on the belt portion 72.

The area of the TENS device which contacts the body of the patient may contain metal or other conductor means forming an integral part of the package to act as electrodes. The metal or other conduction means may be embedded in the casing of the TENS device and are preferably flush with the surface thereof which is placed against the patient's body. The electrode areas are generally spaced and are preferably located as in the other health-like devices illustrated herein for automatic placement and securing of the electrodes in the proper locations against the body of a patient. This provides a particularly compact and easy to operate system since no wires are strung between electrodes and the TENS device and the resulting system should therefore be less prone to damage.

Figure 14:
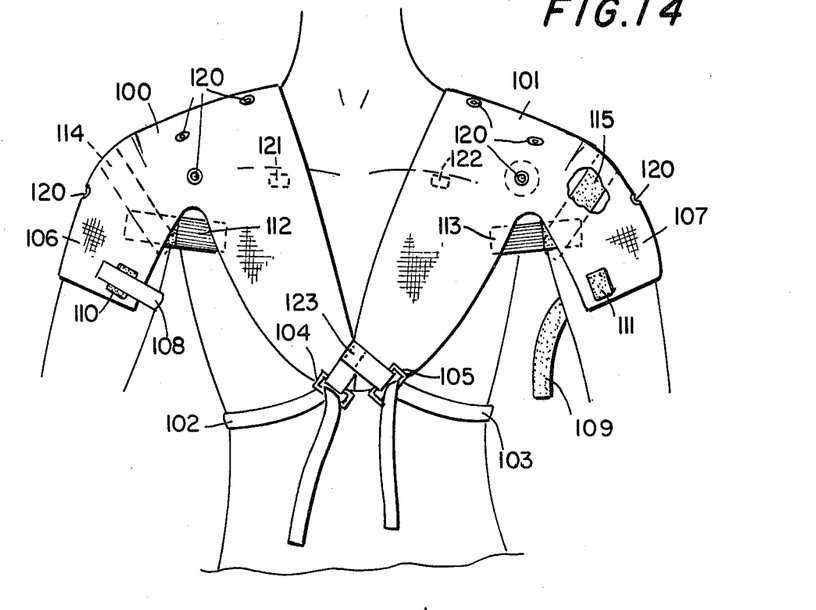
FIGS. 14 and 15 illustrate front and back views, respectively, of another embodiment of the invention.
Figure 15:
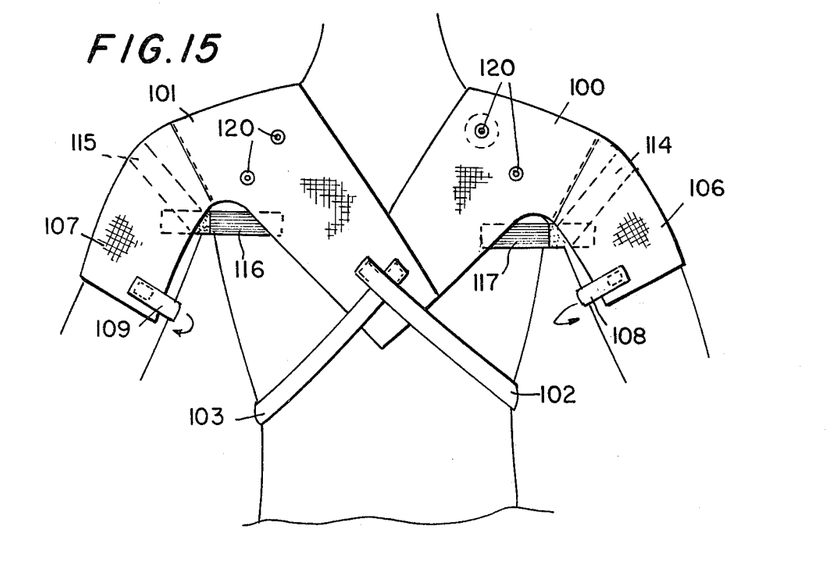

FIGS. 14 and 15 illustrate another embodiment of the invention for use in placing electrodes against the body portion of a wearer in the vicinity of the shoulders, upper arm and upper back area. The device comprises first and second portions 100,101 which are connected together to respectively go over the left and right shoulders of a patient. Straps 102,103 are secured to the rear of the device and connect to the front of the device via respective buckles 104,105 after having passed around the patients body to secure the apparatus in place. The members 100,101 include respective portions 106,107 which extend down the arm of a patient, which portions are retained in position by means of straps 108,109, respectively, which are adjustably connected via Velcro closure devices 110,111 to adjustably secure the device around the patient's arms. Adjustable straps 112,113 are fixedly secured to members 100,101, respectively, and are adjustably connected via Velcro closures 114,115 as indicated in FIG. 14 to adjust the angle between portion 106 and portion 100, and also portions 107 and 101. The rear portion of the device comprises similar adjustable straps 116,117 which engage respective Velcro portions 115,114. If desired, straps 112,113,116,117 may be made of elastic material to provide for more patient comfort. The straps preferably engage interior of the arm portions 106,107.

Figures 16, 18, 19:
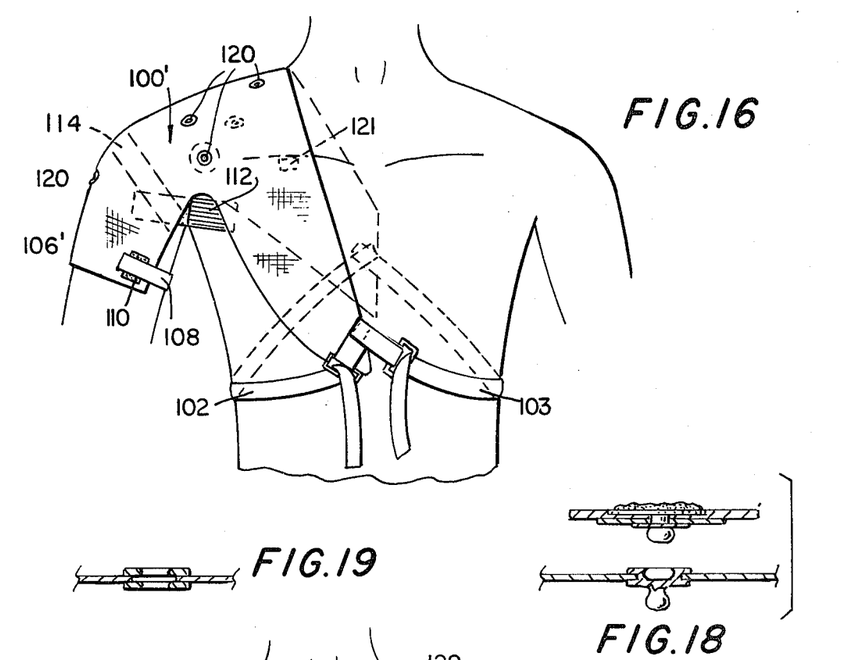
FIGS. 16 and 17 illustrate front and back views, respectively, of another embodiment of the invention.
FIG. 18 shows details of a two-sided snap connector arrangement useful in the present invention.
FIG. 19 illustrates a different type of two-sided snap connector arrangement.

The device has connectors 120 for electrically connecting electrodes to, for example, a TENS device and for fixing electrodes in proper position. For example, the electrical connectors 120 may comprise double-side snaps as illustrated in FIG. 18 or as illustrated in FIGS. 10 and 11. An electrode is preferably snapped to the interior portion of the snap connector 120 to make electrical connection to the electrode and to positively and fixedly locate the electrode on the device. A TENS device or the like is then connected to the other side of the double-sided snap or other electrical connector via an appropriate mating connector to provide electrical energy to the electrode. Electrodes may be placed at any or all of the electrode connectors 120, and electrical connection to an appropriate stimulation device such as a TENS device may be made, as conditions warrant.

The device of FIGS. 14 and 15 comprises locating surface portions 121,122 which may comprise a non-irritating fabric portion which is easily discernible, a protruding portion, or other easily determinable surface portion for location against, for example, a collarbone of the patient to perfectly locate the device on the body of the patient in repeatable and accurately determined positions. Alternatively, the device may be constructed and/or configured so that the buckle portion 123 is locatable at the area of the body corresponding to the dip in the front central portion of a patient's breastbone. Other locating means could be provided, as desired. The locating means 121,122 and/or 123 comprise an important feature of the invention since it permits automatic and accurate electrode location against the body of a patient in such a manner that the patient may easily wear the garment without the aid of a practitioner and produce the desired result.

Figure 17:
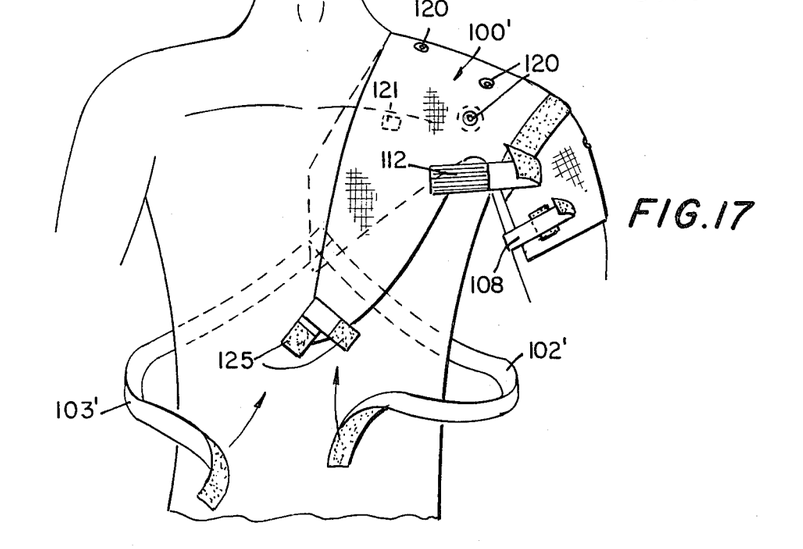

FIGS. 16 and 17 illustrate a modified arrangement. FIG. 16 illustrates a device 100' which is usable over the right shoulder of a patient. Basically, the device of FIG. 16 comprises the left-hand portion of the device of FIG. 14 and identical parts shown therein are not described. This device is suitable for use with a TENS device for making contact with nerve points on the right side of the patient's body. This device is used where stimulation is not required on the left side of the body.

FIG. 17 illustrates the device of FIG. 16 turned inside-out so that it may be used on the left shoulder of the patient. In turning the device inside-out, the straps 108,112 connect on the outside of the device rather than the inside as shown in FIG. 16. Also, the straps 103,102 of FIG. 16 are modified slightly in FIG. 17 as straps 102,103' with Velcro fasteners at the end thereof to adjustably connect with mating Velcro fasteners 125. The Velcro fastening arrangement of FIG. 17 may also be used in the arrangement of FIG. 16. Preferably, the electrical snap-type connectors 120 are symmetrical in that they constitute double-sided male or double-sided female snap-type connectors so that the same electrodes and TENS connecting devices can be used when the garment is either in its normal condition as shown in FIG. 16 or in its inside-out condition as shown in FIG. 17. The locating device 121 is preferably of the type that may felt by the patient from both sides of the device, or it may comprise a fabric or other roughened surface portion attached to both the inside and the outside of the device for accurate location by the patient.

FIG. 19 illustrates a modified two-sided snap connector which is a female snap on both sides thereof. This is a particularly advantageous construction since it enables the device to be turned inside out while maintaining the type of snap connector consistent throughout. The snap connectors of FIGS. 18 and 19 may be used with belt-type devices and electrical connections can be made thereto in a manner similar to that described with respect to FIGS. 14–17. Such a belt device would also be reversible, if desired.

The present invention has been described with respect to two specific types of applications. However, it should be clear that devices of the type to which the present invention pertains may be configured to encircle other body portions, for example arms, legs, thighs, ankles, neck, etc. Suitable locating means could be provided on these various types of devices to locate against predetermined body portions to ensure automatic and accurate electrode placement every time the device is used. In the case of an ankle oriented device, the device may form an L-shaped and be generally in the shape of a conventional ankle brace, but with electrodes, connectors, locators, etc. mounted thereto. Various other modifications and alterations may be made to the present inventive concept within the scope of the appended claims. For example, the embodiment of FIGS. 14–17 can be made completely or partially of elastic material to insure a better fit of the device against the body. Also, the arm portions 106,107 can be eliminated if desired. Still further, the device may be placed with additional tie straps and adjustment straps to provide more flexibility so that the device will fit a greater variety of body shapes.

I claim:

1. A device for continuously fixed automatic anatomically correct placement of at least one electrode means against one or more predetermined portions of a body, said at least one electrode means being adapted to transmit electrical signals, said device comprising:

a substantially non-stretchable first portion adapted to be placed against a body portion of a wearer, said first portion having at least one electrode means at at least one electrode receiving position thereon;

means for electrically connecting said at least one electrode means to an electrical signal generating and/or signal receiving device;

touch-type locating means on said first portion and being cooperable with a given body portion of a wearer, said given body portion of the wearer having touch locatable characteristics, for positively automatically locating said device relative to said given body portion of the wearer, said at least one electrode means being a corresponding substantially fixed distance from said locating means so as to be adjacent said one or more predetermined body portions of the wearer each and every time the device is mounted to the body of the wearer, said one or more predetermined body portions being substantially fixed distances from said given body portion which last mentioned fixed distances are substantially the same as respective first mentioned fixed distances; and means for removably securing said first portion to the body of the wearer with said touch-type locating means adjacent said given body portion of the wearer and with said at least one electrode means adjacent to said one or more predetermined body portions of the wearer.

2. The device of claim 1, wherein said touch-type locating means is a touch sensitive locating means.

3. The device of claim 1 or 2, wherein said first portion is in the general form of a belt which is adapted to encircle a portion of the trunk of a wearer adjacent the lower back of the wearer.

4. The device of claim 1 or 2, wherein said first portion is a belt-like member adapted to encircle at least a portion of the lower trunk of a wearer adjacent the lower back of the wearer, and wherein said locating means comprises means on said first portion for cooperating with the spine of the wearer for locating said device relative to the spine.

5. The device of claim 4 wherein said locating means comprises a protrusion on said first portion.

6. The device of claim 5, wherein said locating means comprises a stiffened portion of said first portion.

7. The device of claim 1 or 2, wherein said locating means comprises a stiffened portion of said first portion.

8. The device of claim 1 or 2, wherein said first portion is adapted to engage at least one shoulder and upper shoulder area portion of a wearer.

9. The device of claim 8, wherein said first portion is adapted to extend down around the upper back and upper breast area of the wearer.

10. The device of claim 9, wherein said electrically connecting means comprises connector elements coupled to said first portion for connecting to said at least one electrode, said connector elements also being adapted to be connected to said electrical signal generating and/or signal receiving device for energizing said electrodes.

11. The device of claim 8, wherein said first portion comprises an inverted generally U-shaped portion and extending portions which extend from said inverted U-shaped portion and which are adapted to extend over the upper arm of the wearer, and further comprising adjusting means coupled to said first portion for adjusting the angle between said inverted U-shaped portion and said extending portions.

12. The device of claim 11, further comprising elongated adjustable strap members coupled to said first portion and adapted to extend from the back to the front of the body, and around each side of the body of the wearer, for securing said device to the body of the wearer.

13. The device of claim 12, further comprising strap connecting means coupled to said first portion for fixedly locating said portions extending over the arms of the wearer to the arms of the wearer.

14. The device of claim 8, wherein said locating means positively locates said device relative to said the upper body portion of a wearer.

15. The device of claim 14, wherein said locating means comprises a locating element adapted to engage the collarbone area of a patient.

16. The device of claim 14, wherein said locating means comprises means adapted to engage a specified area of the breastbone of the wearer.

17. The device of claim 8, wherein said first portion and said means for removably securing said first portion to the body of the wearer together comprise means for encircling a body portion of a wearer.

18. The device of claim 1 wherein said electrically connecting means comprises one or more elongated wires mounted to said first portion; and respective connecting elements coupled to said first portion and to the ends of said wires for selective and removable connection to at least one electrode means.

19. The device of claim 18 wherein said first portion comprises first and second layers, and wherein said wires extend between said layers.

20. The device of claim 18, wherein said connecting elements comprise receptacles.

21. The device of claim 18, wherein said connecting elements comprise snap-like connectors.

22. The device of claim 18, wherein said first portion is in the general form of a belt which is adapted to encircle a portion of the trunk of a wearer adjacent the lower back of the wearer.

23. The device of claim 1, wherein said electrically connecting means comprises connecting elements on said first portion for engaging and electrically contacting said at least one electrode means and means coupled to said connecting elements for electrically connecting said connecting elements to said electrical signal generating and/or receiving device.

24. The device of claim 1, wherein said first portion comprises said electrical signal generating and/or receiving device, said first portion also comprising said means for electrically connecting said at least one electrode means to said electrical signal generating and/or receiving device.

25. The device of claim 24, wherein said at least one electrode means is an integral part of said electrical signal generating and/or receiving device and comprises at least one electrical contact member on the surface of said electrical signal generating and/or receiving device.

26. The device of claim 24 or 25, wherein said first portion comprises at least part of a member which is adapted to encircle a body portion of a wearer.

27. The device of claim 26, wherein said member which is adapted to encircle a body portion of the wearer comprises a belt-type member adapted to encircle a portion of the trunk of a wearer.

28. The device of claim 26, wherein said electrical signal generating and/or receiving device is flexible to conform to body contours of a wearer.

29. The device of claim 28, wherein said electrical signal generating and/or receiving device is integrally connected with, and forms a part of, said member which is adapted to encircle a body portion of a wearer.

30. The device of claim 24 or 25, wherein said electrical signal generating and/or receiving device is integrally formed with said first portion and with said means for removably securing said first portion to the body of the wearer.

31. The device of claim 24 or 25, wherein said electrical signal generating and/or receiving device is flexible to conform to body contours of a wearer.

32. The device of claim 1 or 2, wherein said first portion has a plurality of electrode receiving positions thereon, and comprises at least one of said electrode means at at least one of said electrode receiving positions.

33. The device of claim 1 or 2, wherein said first portion and said means for removably securing said first portion to the body of the wearer together comprise means for encircling a body portion of a wearer.

* * * * *